United States Patent
Gorochow et al.

(10) Patent No.: US 10,939,915 B2
(45) Date of Patent: Mar. 9, 2021

(54) ANEURYSM DEVICE AND DELIVERY SYSTEM

(71) Applicant: DePuy Synthes Products, Inc., Raynham, MA (US)

(72) Inventors: Lacey Gorochow, Raynham, MA (US); Ariel Soto Del Valle, Raynham, MA (US); Juan Lorenzo, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 154 days.

(21) Appl. No.: 15/993,903

(22) Filed: May 31, 2018

(65) Prior Publication Data
US 2019/0365385 A1    Dec. 5, 2019

(51) Int. Cl.
*A61B 17/12* (2006.01)
*A61B 17/00* (2006.01)

(52) U.S. Cl.
CPC .. *A61B 17/12113* (2013.01); *A61B 17/12168* (2013.01); *A61B 17/0057* (2013.01); *A61B 2017/00623* (2013.01)

(58) Field of Classification Search
CPC .......... A61B 17/0057; A61B 17/12031; A61B 17/12113; A61B 17/12168; A61B 17/12172; A61B 2017/00623; A61B 2017/12054
USPC ........................................................ 606/198
See application file for complete search history.

(56) References Cited

U.S. PATENT DOCUMENTS

| | | |
|---|---|---|
| 2,849,002 A | 8/1958 | Oddo |
| 3,480,017 A | 11/1969 | Shute |
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |

(Continued)

FOREIGN PATENT DOCUMENTS

| | | |
|---|---|---|
| CA | 2395796 A1 | 7/2001 |
| CA | 2598048 A1 | 5/2008 |

(Continued)

OTHER PUBLICATIONS

Altes et al., Creation of Saccular Aneurysms in the Rabbit: A Model Suitable for Testing Endovascular Devices. AJR 2000; 174: 349-354.

(Continued)

*Primary Examiner* — Katherine M Shi
*Assistant Examiner* — Alyssa M Keane
(74) *Attorney, Agent, or Firm* — Troutman Pepper Hamilton Sanders LLP

(57) ABSTRACT

The present disclosure relates to a braid for treating an aneurysm. The braid can include a distal end opposite a proximal end. Translating the braid can cause the delivery portion to expand and form a distal sack as well as invert into itself.

15 Claims, 9 Drawing Sheets

(56) References Cited

U.S. PATENT DOCUMENTS

| | | |
|---|---|---|
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Chin et al. |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford et al. |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones et al. |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |

(56) References Cited

U.S. PATENT DOCUMENTS

| | | |
|---|---|---|
| 9,675,782 B2 | 6/2017 | Connolly |
| 9,676,022 B2 | 6/2017 | Ensign |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2* | 3/2018 | Marchand ........ A61B 17/12177 |
| 9,955,976 B2 | 5/2018 | Hewitt et al. |
| 10,130,372 B2 | 11/2018 | Griffin |
| 10,307,148 B2 | 6/2019 | Helsel et al. |
| 10,327,781 B2 | 6/2019 | Divino et al. |
| 10,342,546 B2 | 7/2019 | Sepetka et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0281350 A1 | 11/2008 | Sepetka |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0324649 A1 | 12/2010 | Mattsson |
| 2011/0046658 A1 | 2/2011 | Connor et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0345738 A1 | 12/2013 | Eskridge |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1* | 5/2014 | Divino ..................... A61F 2/95 606/194 |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1* | 3/2017 | Rhee ................ A61B 17/12172 |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang |

(56) References Cited

U.S. PATENT DOCUMENTS

| | | |
|---|---|---|
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0328398 A1 | 10/2019 | Lorenzo |
| 2019/0365385 A1 | 12/2019 | Gorochow et al. |

FOREIGN PATENT DOCUMENTS

| | | |
|---|---|---|
| CA | 2 431 594 A1 | 9/2009 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | 9641589 A1 | 12/1996 |
| WO | 99/05977 A1 | 2/1999 |
| WO | 9908607 A1 | 2/1999 |
| WO | 99/30640 A1 | 6/1999 |
| WO | 2003073961 A1 | 9/2003 |
| WO | 2005020822 A1 | 3/2005 |
| WO | 2005/074814 A2 | 8/2005 |
| WO | 2005117718 A1 | 12/2005 |
| WO | 2006034149 A2 | 3/2006 |
| WO | 2006052322 A2 | 5/2006 |
| WO | 2007/076480 A2 | 7/2007 |
| WO | 2008150346 A1 | 12/2008 |
| WO | WO 2008151204 A1 | 12/2008 |
| WO | 2009048700 A1 | 4/2009 |
| WO | 2009105365 A1 | 8/2009 |
| WO | 2009132045 A2 | 10/2009 |
| WO | 2009135166 A2 | 11/2009 |
| WO | 2010030991 A1 | 3/2010 |
| WO | 2011057002 A2 | 5/2011 |
| WO | 2012032030 A1 | 3/2012 |
| WO | 2012099704 A2 | 7/2012 |
| WO | 2012099909 A2 | 7/2012 |
| WO | 2012113554 A1 | 8/2012 |
| WO | 2013016618 A2 | 1/2013 |
| WO | 2013025711 A1 | 2/2013 |
| WO | 2013109309 A1 | 7/2013 |
| WO | 2013159065 A1 | 10/2013 |
| WO | 2014029835 A1 | 2/2014 |
| WO | 2014110589 A1 | 7/2014 |
| WO | 2014137467 A1 | 9/2014 |
| WO | 2015073704 A1 | 5/2015 |
| WO | 2015160721 A1 | 10/2015 |
| WO | 2015166013 A1 | 11/2015 |

(56) References Cited

FOREIGN PATENT DOCUMENTS

| WO | 2015171268 A1 | 11/2015 |
| WO | 2015184075 A1 | 12/2015 |
| WO | 2015187196 A1 | 12/2015 |
| WO | 2016/044647 A2 | 3/2016 |
| WO | 2016107357 A1 | 7/2016 |
| WO | 2016/137997 A1 | 9/2016 |
| WO | 2018/051187 A1 | 3/2018 |

OTHER PUBLICATIONS

Schaffer, Advanced Materials & Processes, Oct. 2002, pp. 51-54.
Extended European Search Report issued in corresponding European Patent Application No. 19 21 5277 dated May 12, 2020.

\* cited by examiner

- 805: selectively positioning a braid at or adjacent a neck of the aneurysm
- 810: distally sliding the braid into the aneurysm
- 815: radially expanding a distal segment of the braid to form an occlusive sack inside the aneurysm, the occlusive sack configured to occlude the aneurysm
- 820: further distally sliding the braid into the aneurysm thereby buckling the distal segment buckle about the neck of the aneurysm
- 825: further distally sliding the braid into the aneurysm thereby inverting a central segment of the braid into the distal segment
- 830: tucking a proximal segment of the braid into the central segment
- 835: releasing the braid within the aneurysm

905 — positioning a delivery tube within a microcatheter

910 — positioning a braid with the delivery tube, the braid being in a collapsed state with the microcatheter 915 — selectively positioning the microcatheter, the delivery tube, and the braid at or adjacent the neck of the aneurysm 920 — distally sliding the braid, by the delivery tube, from the microcatheter into the aneurysm 925 — radially expanding a distal segment of the braid to form an occlusive sack inside the aneurysm, the occlusive sack configured to occlude the aneurysm 930 — further distally sliding the braid, by the delivery tube, thereby buckling the distal segment about the neck of the aneurysm 935 — further distally sliding the braid, by the delivery tube, thereby inverting a a central segment of the braid proximal the distal segment into the occlusive sack 940 — tucking a proximal segment proximal the central segment into the central segment 945 — releasing the braid within the aneurysm and withdrawing the delivery tube and the microcatheter from the aneurysm

ANEURYSM DEVICE AND DELIVERY SYSTEM

FIELD

This disclosure relates to medical instruments, and more particularly, delivery systems for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the brain tissue surrounding cranial vessels the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the braid and its nerves. Furthermore, embolic coils do not always effectively treat aneurysms as re-canalization of the aneurysm and/or coil compaction can occur over time.

One particular type of occlusive approach endeavors to deliver and treat the entrance or "neck" of the aneurysm as opposed to the volume of the aneurysm by implanting a device in the parent vessel of the aneurysm. In such "neck" approaches, by minimizing blood flow across the neck, a cessation of flow into the aneurysm may be achieved. In turn, a thrombotic mass may naturally form without having to deliver embolic materials into the aneurysm sac, as previously described. This approach is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches, such as implanting a flow impeding device in the parent vessel, are not without drawbacks. This type of approach may impede blood flow into peripheral blood vessels while blocking the aneurysm neck in the parent vessel. Impeding flow to the peripheral blood vessel can unintentionally lead to severe damage if the openings of the vessels are blocked.

The solution of this disclosure resolves these and other issues of the art.

SUMMARY

In some embodiments, the present disclosure relates to a braid for treating an aneurysm. The braid can include a proximal end and a distal end. The braid can also include a distal segment disposed about the distal end. The distal segment can be configured to transition from a collapsed state within a microcatheter to a deployed state distal of the microcatheter whereby the distal segment has radially expanded to form a distal sack. A central segment can be disposed in communication with the distal segment. The central segment can be capable of inverting into the distal sack. A proximal segment can be disposed in communication with the central segment and disposed about the proximal end. The proximal segment can be capable of being tucked into the central segment in the deployed state. Each of the proximal, distal, and central segments can have a different porosity and/or a different flexibility.

In some embodiments, the distal, central, and proximal segments are formed from a single monolithic structure.

In some embodiments, the distal, central, and proximal segments are discrete connected components of a single mesh.

In some embodiments, an inflection point is disposed between the central segment and the distal segment. The proximal end of the braid can be configured to be tucked inside the distal sack in the deployed state until the central segment is inverted so the inflection point is disposed adjacent the neck of the aneurysm to induce a flow diverting effect.

In some embodiments, a braid for treating an aneurysm is disclosed. The braid can include a proximal end and a distal end. The braid can also include a distal segment disposed about the distal end, the distal segment operable to transition from a collapsed state within a microcatheter to a deployed state distal of the microcatheter whereby the distal segment radially expands to form a distal sack. A proximal segment can be disposed about the proximal end, wherein the proximal segment is capable of inverting and being tucked into the distal sack.

In some embodiments, the proximal segment includes a porosity greater than a porosity of the distal segment, or vice versa. The proximal end can be configured to be tucked inside the distal sack in the deployed state until a proximal end of the distal segment is disposed adjacent the neck of the aneurysm to induce a flow diverting effect. The distal sack can also be spherical, though the braid is not so limited and its distal sack can take any shape as needed or required. The distal segment can include a flexibility greater than a flexibility of the proximal segment, or vice versa.

In some embodiments, the braid can also include an inflection point disposed between the proximal and distal segments. The proximal segment can also be configured to be inverted when the inflection point is distal of the microcatheter. The proximal segment can be configured to be inverted by the inflection point when the braid has been translated distally a predetermined distance with respect to the microcatheter and/or the aneurysm.

In some embodiments, the proximal segment is configured to be inverted into the distal segment as the braid is distally pushed deeper into the aneurysm. The proximal segment can be configured to be inverted into the distal segment in a "tube-sock" manner.

In some embodiments, the distal sack has a diameter at least two times greater than the microcatheter. However, the diameter of the distal sack in the deployed state can be larger or smaller, as needed or required according to the particular aneurysm being occluded.

In some embodiments, the braid can include a central segment disposed between the proximal and distal segments. Each of the proximal, distal, and central segments can include a different flexibility. The central segment can include a flexibility greater than a flexibility of the proximal and distal segments. The flexibility of the distal segment can be greater than the flexibility of the proximal segment. In some embodiments, in the deployed state, at least some of the central segment can be tapered where the central segment communicates with the distal segment.

In some embodiments, each of the proximal, distal, and central segments comprise a different porosity. The central segment can include a porosity greater than a porosity of the proximal and distal segments. The porosity of the distal segment can be greater than the porosity of the proximal segment. The central segment can be configured for positioning on or adjacent the neck of the aneurysm in the deployed state to induce a flow diverting effect.

In some embodiments, a first inflection point can be disposed between the distal segment and the central segment and a second inflection point can be disposed between the central segment and the proximal segment. In the deployed state, the first inflection point is configured to cause the proximal end of the distal segment to buckle when the braid is distally translated a first distance. In the deployed state, the second inflection point is configured to cause the central segment to invert into the distal segment when the braid is distally translated a second distance. In other embodiments, in the deployed state, the first inflection point is configured to cause the proximal end of the distal segment to buckle about the neck of the aneurysm and the second inflection point is configured to cause the central segment to invert into the distal segment. In other embodiments, when the first inflection point is distal of the microcatheter (e.g. inside the aneurysm), the first inflection point is configured to cause the proximal end of the distal segment to buckle about the neck of the aneurysm and when the second inflection point is distal of the microcatheter, the second inflection point is configured to cause the central segment to invert into to the distal segment and the proximal segment tuck into the central segment.

In some embodiments, the proximal and/or central segment are/is configured to be tucked inside the distal sack in the deployed state until the first inflection point is disposed adjacent the neck of the aneurysm to induce a flow diverting effect. The proximal segment and the central segment can also be configured to be inverted into the distal segment in a "tube-sock" manner.

In some embodiments, an occlusive system for treating an aneurysm is disclosed. The system can include a microcatheter and a delivery tube translatably disposed in the microcatheter. A braid can also be included and connected the braid being detachably connected to the delivery tube (e.g. a locking portion disposed at the proximal end of the braid detachably connected to the distal end of the delivery tube) and slideably disposed within the microcatheter in a collapsed state and distally translatable from within the microcatheter to a deployed state distal of the microcatheter in the aneurysm. The braid can expand, including the distal, central and/or proximal expandable segments, to the deployed state as the distal end of the braid distally exits the microcatheter, contacts the aneurysm wall, and/or is otherwise disposed inside the aneurysm, distal of the microcatheter.

In some embodiments, translating the braid distally away from the microcatheter causes the central segment to invert into the distal sack and the proximal segment to tuck in the central segment. In some embodiments, the central segment can include a porosity greater than a porosity of the proximal and distal segments. The porosity of the distal segment can be greater than the porosity of the proximal segment. The central segment can be configured for positioning on or adjacent the neck of the aneurysm in the deployed state to induce a flow diverting effect.

In some embodiments, in the deployed state, the braid is detachable from the microcatheter and/or the delivery tube in the aneurysm.

In some embodiments, the system can also include radiopaque entities such as platinum wires woven into the braid, or drawn filled tube wires with platinum so that the device can be imaged under fluoroscopy. Including these entities will allow the user to understand and visualize the location of the distal sack with respect to the aneurysm. The orientation and/or a position of the distal sack or any other feature of the braid, is adjustable by the braid being distally or proximally moved by the delivery tube.

In some embodiments, the system can also include an imaging device operatively connected to the occlusive device. The imaging device is capable of imaging the distal sack with respect to the aneurysm so that an orientation and/or a position of the distal sack, or any other feature of the braid, is adjustable by the braid being distally or proximally moved by the delivery tube.

In some embodiments, a method of occluding an aneurysm is disclosed. The method can include selectively positioning a braid at or adjacent a neck of the aneurysm; distally sliding the braid into the aneurysm; radially expanding a distal segment of the braid to form a distal sack inside the aneurysm, the distal sack configured to occlude the aneurysm; further distally sliding the braid into the aneurysm thereby buckling the distal segment buckle about the neck of the aneurysm; further distally sliding the braid into the aneurysm thereby inverting a central segment of the braid into the distal segment; tucking a proximal segment of the braid into the central segment; and releasing the braid within the aneurysm.

In some embodiments, the method can include tucking the proximal segment into the central segment until an inflection point between the distal segment and the central segment is adjacent or in communication with the neck of the aneurysm; and inducing a flow diverting effect across the neck of the aneurysm. In some embodiments, during said tucking, the distal segment does not move relative to the distal segment.

In some embodiments, the method can include positioning a first inflection point between the distal segment and the central segment; positioning a second inflection point between the central segment and the proximal segment; buckling the distal segment about the neck of the aneurysm, by the first inflection point, when distally translating a proximal end of the braid a first distance with respect to the neck of the aneurysm; and inverting the central segment into the distal segment, by the second inflection point, by distally translating the proximal end of the braid a second distance with respect to the neck of the aneurysm. In some embodiments, inverting the central segment into the distal segment, by the second inflection point, causes the central segment to taper into the distal segment. The tapered portion between the central and distal segments can also be disposed on or adjacent the neck of the aneurysm in the deployed state.

In some embodiments, the method can include forming the central segment with a porosity greater than a porosity of the proximal and distal segments; and forming the porosity of the distal segment greater than the porosity of the proximal segment.

In some embodiments, a method of occluding an aneurysm is disclosed. The method can include positioning a braid with the delivery tube, the braid being in a collapsed state with the microcatheter; selectively positioning the microcatheter, the delivery tube, and the braid at or adjacent the neck of the aneurysm; distally sliding the braid, by the delivery tube, from the microcatheter into the aneurysm; radially expanding a distal segment of the braid to form a distal sack inside the aneurysm, the distal sack configured to occlude the aneurysm; further distally sliding the braid, by the delivery tube, thereby buckling the distal segment about the neck of the aneurysm; further distally sliding the braid, by the delivery tube, thereby inverting a central segment of the braid proximal the distal segment into the distal sack; tucking a proximal segment proximal the central segment into the central segment; and releasing the braid within the aneurysm and withdrawing the delivery tube and the microcatheter from the aneurysm.

In some embodiments, the method can include positioning a first inflection point between the distal segment and the central segment; positioning a second inflection point between the central segment and the proximal segment; buckling the distal segment about the neck of the aneurysm, by the first inflection point, when distally translating a proximal end of the braid a first distance with respect to the neck of the aneurysm; and inverting the central segment into the distal segment, by the second inflection point, by distally translating the proximal end of the braid a second distance with respect to the neck of the aneurysm.

In some embodiments, inverting the central segment into the distal sack creates a flow diverting effect across the neck of the aneurysm.

In some embodiments, the method can include forming each of the proximal, distal, and central segments with a different porosity.

In some embodiments, the method can include forming the central segment with a porosity greater than a porosity of the proximal and distal segments; and forming the porosity of the distal segment greater than the porosity of the proximal segment.

In some embodiments, the method can include tucking the proximal segment into the central segment until the central segment is adjacent or in communication with the neck of the aneurysm; and inducing a flow diverting effect across the neck of the aneurysm.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 8 is a flow diagram for a method of delivering an occlusive device.

FIG. 9 is a flow diagram for a method of delivering an occlusive device.

DETAILED DESCRIPTION

Figure 1:
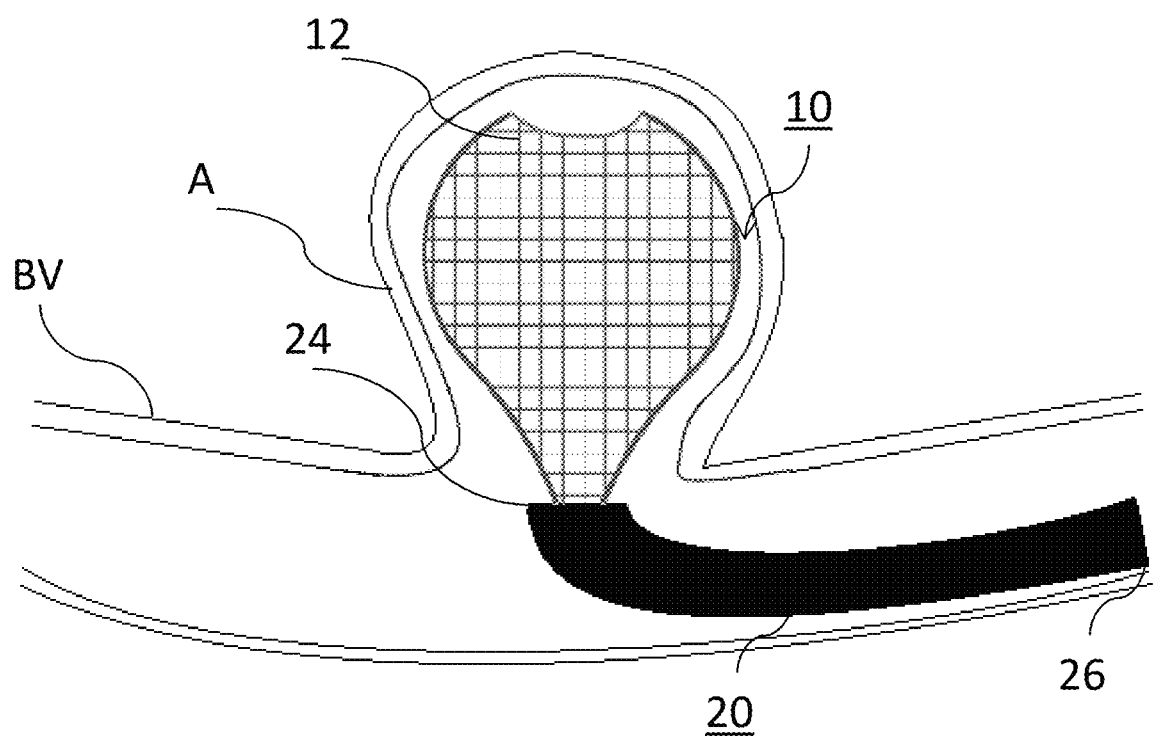
FIG. 1 depicts an example occlusive device of this disclosure partially deployed into an aneurysm.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Figure 2:
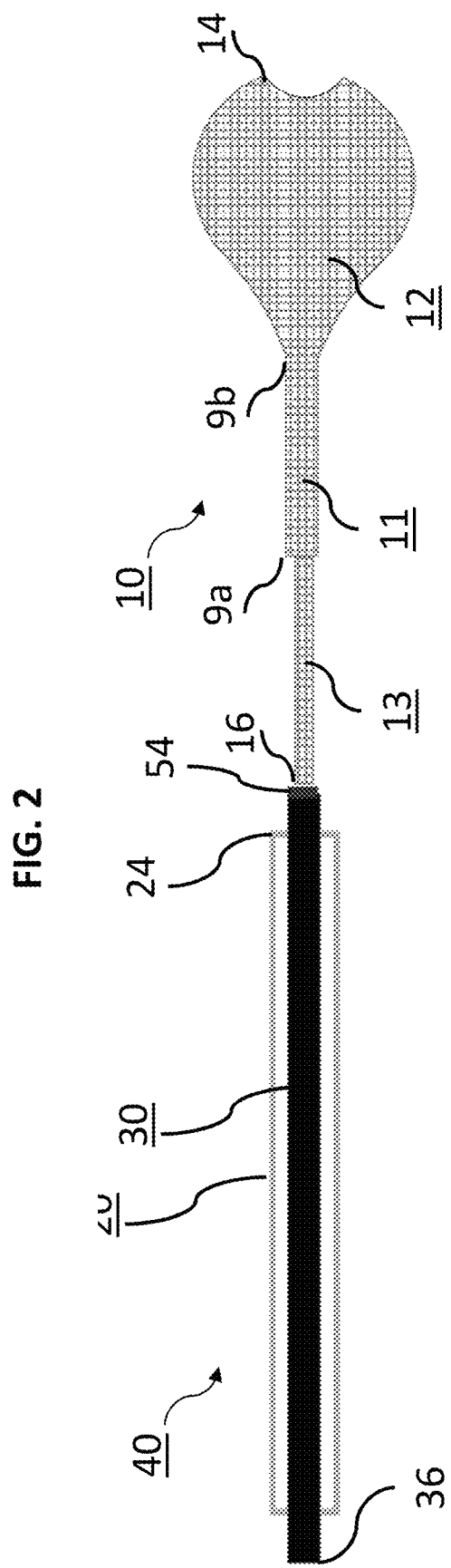
FIG. 2 is a schematic side view of an exemplary delivery system with an occlusive device in communication with, and deployed from, a microcatheter.

Turning to FIG. 1, an example braid 10 of this disclosure is shown deployed into an aneurysm A of blood vessel BV but not yet released from the microcatheter 20, including delivery tube 30 that is disposed therein, which is shown more clearly in FIG. 2. Braid 10 addresses the drawbacks of coils by being a single device configured to treat the aneurysm A and improves the sealing of the aneurysm neck. In FIG. 1, the microcatheter 20 has been delivered to the neck of the aneurysm A and a distal sack has formed by a distal segment 12 of braid 10. Braid 10 is shown forming a predetermined shape and structure configured to outline, and support the walls of the aneurysm A.

The size of the microcatheter 20 shown in FIG. 1 is selected in consideration of the size, shape, and directionality of the aneurysm or the body lumens the catheter must pass through to get to the treatment site. The microcatheter 20 may have a total usable length anywhere from 80 centimeters to 170 centimeters. The microcatheter 20 may have an inner diameter ID of anywhere between 0.015 and 0.032 inches. The outer diameter OD may also range in size and may narrow at either its proximal end or distal end. At its proximal end 26, the microcatheter 20 may be manually operated by the end-user, and at its distal end 24 may be operable, as illustrated, to be positioned at the neck of the aneurysm A. While the distal end 24 of the microcatheter 20 can contain the braid 10, the end 24 may be varied in shape and may curve at an angle.

Turning to FIG. 2, a schematic side view is shown of braid 10 when connected with delivery tube 30 and being deployed from microcatheter 20 in a deployed configuration but prior to being positioned in aneurysm A. The delivery tube 30 can be capable of being distally pushed through the microcatheter 20. Delivery tube 30 can be substantially elongate and can extend from the proximal 26 to the distal end 24 of microcatheter 20. Tube 30 can generally run along the inner lumen of microcatheter 20 and may leave a space between its outer surface and the internal surface of microcatheter 20. In turn, delivery tube 30 and microcatheter 20 may be axially aligned. Delivery tube 30 and microcatheter 20 together can deliver braid 10 to a location of interest (e.g. a lesion site). In certain embodiments, microcatheter 20 can be pre-placed at a level of the aneurysm neck and used to track braid 10 to the lesion. Delivery tube 30 can be in mechanical connection with braid 10 at locking portion 54. Braid 10 may be attached to locking portion 54 by slidable attachment, permanent attachment (e.g. crimped, laser, ultrasonic weld, or other sources of heat, adhesive, or the like) or other detachable attachment approaches. When delivery tube 30 is mechanically attached to braid 10 at locking portion 54, distally translating, sliding, or otherwise moving tube 30 towards the aneurysm A can cause braid 10 to begin moving from a collapsed state within microcatheter 20 to a deployed state external to microcatheter 20 with distal sack of braid 10 for occluding aneurysm A, as discussed more particularly below.

Braid 10 can include an open distal end 14 and a proximal end 16. Braid 10 can be formed from a self-expanding and invertible multi-filament structure that includes a tubular mesh or braid. The distal sack of braid 10 can be formed during deployment as distal end 14 of braid 10 slides out of microcatheter 20 and enters the aneurysm A. The mesh of braid 10 can be defined by one or more mesh patterns with mesh openings defined by braided filaments. The mesh of braid 10 can be made of several materials such as deposited thin films. The mesh of braid 10 can include multiple wires, for example, from 4 to 96 wires. The number of wires, angle of wires, and diameter of the wires, can all be factors in controlling material properties of the braid 10, including porosity and flexibility.

The deployed state of braid 10, including the distal sack of segment 12, can be formed by braid 10 being distally translated from a collapsed state within microcatheter 20 and attached to delivery tube 30 and then being deployed into the aneurysm A, distal of the microcatheter 20. The mesh of braid 10 is configured so that as braid 10 is distally translated and end 14 exits from within microcatheter 20, portions of braid 10, including distal segment 12, can begin to radially expand. As braid 10 is further translated, the segments of braid 10 proximal of segment 12, including central segment 11 and/or proximal segment 13, can also begin expanding, buckling, and/or be caused to invert into braid 10, when inside aneurysm A. The wires can be made from multiple alloys such as a nickel-titanium alloy, cobalt chromium alloys, platinum, nitinol, stainless steel, tantalum, or other alloys, or any other suitable biocompatible materials, or combination of these materials. Also, these materials can be absorbable or non-absorbable by the patient over time. In some embodiments, some or all of braid 10 can be a multi-filament cylindrical mesh made preferably of nitinol with interwoven platinum filaments for radiopacity, or Drawn Filled Tube (DFT) Nitinol with 10 to 40% platinum. The apertures in the mesh of braid 10 can also create a substantially unitary frame work or mesh. Thus, the apertures may be of any size, shape, or porosity, and may be uniformly or randomly spaced throughout the wall of the mesh of braid 10. The apertures can provide the tubular element of braid 10 with flexibility and also assist in the transformation of the mesh from the collapsed state to the expanded, deployed state, and vice versa.

Figure 3:
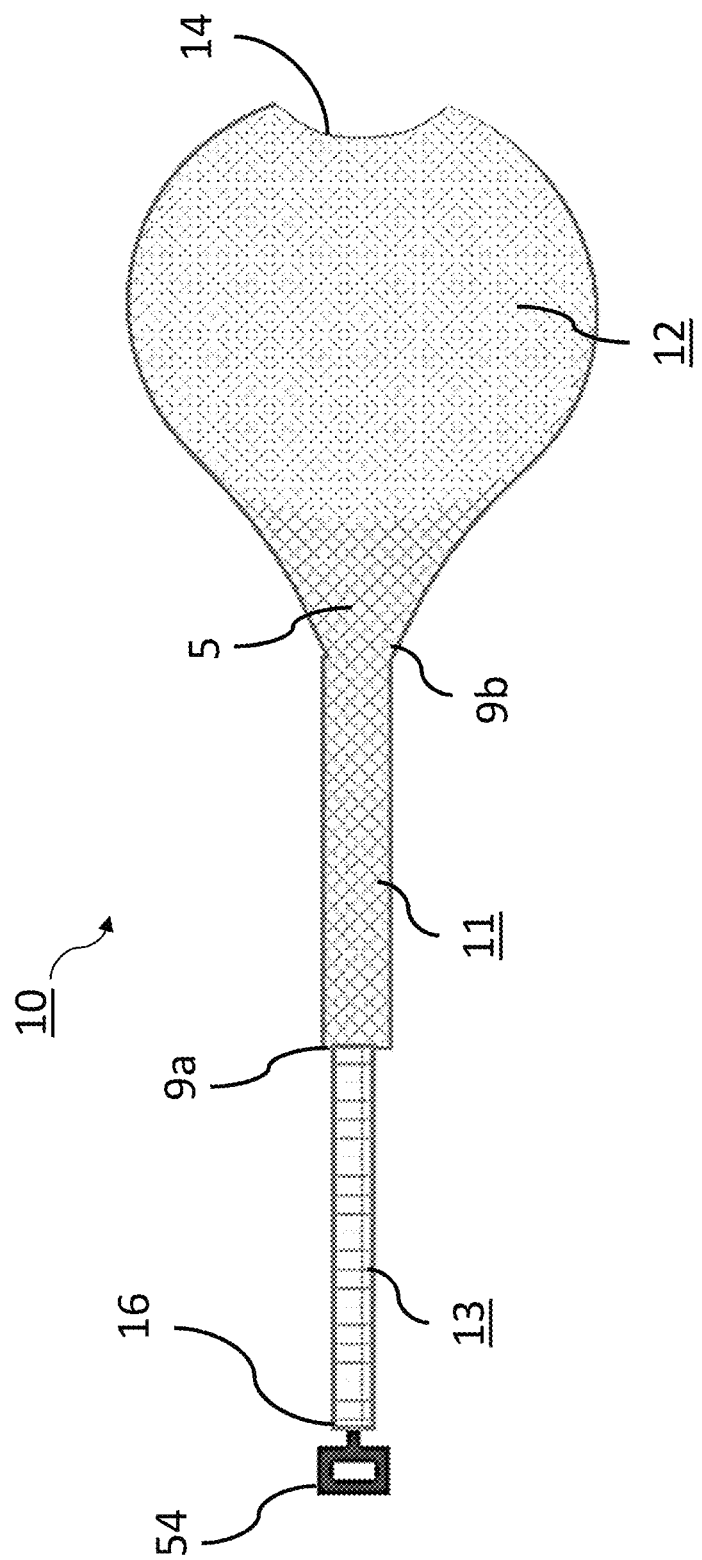
FIG. 3 is an enlarged schematic side view of the braid of FIGS. 1-2 in an expanded state.

Turning to FIG. 3, an enlarged schematic side view of the braid 10 of FIGS. 1-2 is shown in a close-up, expanded state. Other portions of the mesh of braid 10 can have different porosities and/or other material properties, including segments 11 and 13 of braid 10. The braid 10 can include several segments, including a generally spherical shaped distal sack associated with segment 12 in the deployed state. Central segment 11 can be in communication with segment 12 and be tapered as it communicates from a relatively elongate portion adjacent segment 13 to the distal sack of segment 12. In other words, segment 11 can include a tapered portion and an elongate, tubular portion where segment 11 communicates with segment 13. Segment 13 in turn can be substantially elongate and extend proximally from segment 11 to locking portion 54 and/or delivery tube 30, when assembled with microcatheter 20. Segment 13 can have the same diameter as the proximal end of segment 11 or segment 13 can also have a smaller diameter than segment 11. In this respect, braid 10 can include three porous segments, including segments 11, 12, and 13, and each of segments 11, 12, and 13 can have varying flexibility and/or porosity. For example, segment 11, including its tapered portion, can be relatively soft and flexible whereas segment 11 where it communicates with segment 13 can be less flexible with a lower porosity. Varying flexibility and/or porosity in this manner can induce segment 12 to buckle and/or cause segment 11 to invert on itself like a sock as its proximal, stiffer end is distally pushed further into the distal sack of segment 12.

Segment 11 of the braid 10 can have porosity less than the porosity of segment 13 and/or the segment of sack 12. The porosities associated with segments 11, 12, 13 and/or any other region or segment of braid 10 can include filaments having a different shape than the filaments in the other porosity regions. Segment 13 of the braid 10 similarly can have a porosity or flexibility that differs with those of segments 11 and 13. For example, the porosity of segment 13 can be less than porosities of segment 11 and/or 12. Segment 13 may also be less flexible than segment 11 and/or segment 12 in order to induce braid 10 inversion during delivery and inversion as braid 10 deploys and expands within aneurysm A. Braid 10 can also be made from nitinol with interwoven platinum filaments for radiopacity. Varying properties of segments 11, 12, and 13 can allow the braid 10 to invert on itself (like a sock) as braid 10 is deployed in the aneurysm A.

To facilitate inversion of the braid 10, including inversion of segment 11 into segment 12, the braid 10 can be modified to weaken segment 12 (e.g. by facilitating buckling of segment 12 after formation of the distal sack inside aneurysm A) or otherwise make segment 11 more likely to invert. For example, braid 10 can include an inflection point 9a and/or 9b disposed between segments 11 and 12 (9b) and/or between segments 11 and 13 (9a) communicate with each other. Inflection points 9a and/or 9b can be a localized region or can function as a border or separation between each adjoining segment. Inflection point 9a and/or 9b can be a pre-weakened area that induces buckling or inversion of braid 10, as needed or required. Braid 10 is not so limited, however, and other properties can be modified to induce inversion, including a localized braid angle change, removal of wire segments over the tapered area of segment 11, and/or a localize heat treatment to change braid properties. As illustrated, segments 11, 12, and 13 can be configured so that segment 12 can be caused to buckle about the neck of the aneurysm during deployment so that segment 11 can be inverted into segment 12. This novel braid 10 is particularly advantageous as buckling of segment 12 serves as a safety mechanism that prevents segment 12 from expanding too much and risking rupture of aneurysm A. Inverting segment 11 on or adjacent the neck of the aneurysm A can in turn induce a flow diverting effect across the neck of the aneurysm A. This is because segment 13 can be in communication with the neck of the aneurysm when braid 10 is inverted and deployed in the aneurysm, since end 16 can be tucked into segment 12 (e.g., see FIG. 5B).

In certain embodiments, a braid angle of one or some of the segments 11, 12, 13 of braid 10 can vary with respect to a longitudinal axis of the braid 10. The wire diameter, pick count (i.e. the number of wire crossovers per lineal measurement) of braid 10 can also vary or otherwise be modified between segments of braid 10 to change the device characteristics as well as the heat set shape. The diameter of the braid 10 in the deployed state, including the expanded diameter of the distal sack of segment 12, and the braid wire count can vary depending of the distal sack diameter needed to treat the aneurysm A. However, braid 10 is not so limited and it can have a braid angle, pitch count, wire diameter, porosity or any other property of braid 10 that is substantially similar throughout. The fibers of braid 10 can be formed by being fastened at their free ends at end 16 by heat bonding by laser or ultrasonic weld, solvent or adhesive binding, crimping, or any other attachment means. The fibers of each segment of braid 10 may be bonded at their internal crossover points by solvent, adhesive, or heat bonding like laser, ultrasonic weld, or any other source of heat to decrease the flexibility in certain segments of braid 10.

Figure 4A:
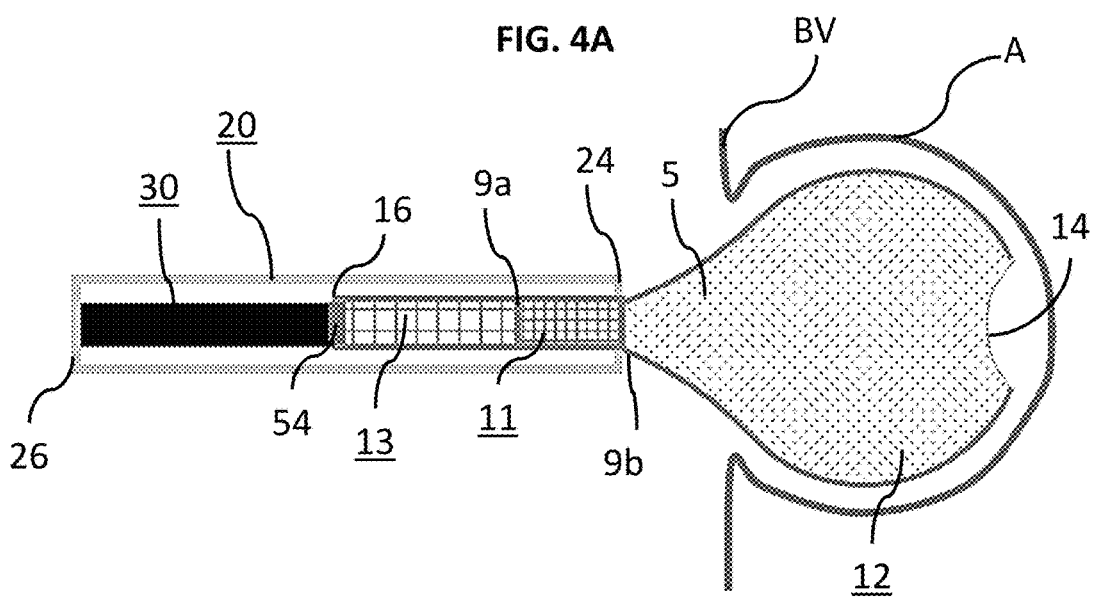
FIG. 4A is an enlarged schematic side view of the delivery system and braid of FIGS. 1-3 as the braid is being continually pushed into an example aneurysm.

FIGS. 4A to 5B depict an enlarged schematic side view of braid 10 attached to delivery tube 30 and partially disposed in microcatheter 20 as the braid 10 is being pushed from microcatheter 20 into an example aneurysm A. The outer diameter of segment 12 is illustrated in FIGS. 4A to 5B radially expanding to a diameter greater than the microcatheter 20 as the distal sack is formed (e.g., greater than twice the diameter of the microcatheter 20). As illustrated in FIG. 4A, segment 12 of braid 10 has expanded from being in a collapsed state disposed inside microcatheter 20 to a deployed state, distal of the microcatheter 20 and beginning to form the distal sack of segment 12 inside aneurysm A. The assembly between microcatheter 20, delivery tube 30, and/or braid 10 can take place before being introduced into the vasculature. the distal sack of segment 12 is illustrated radially expanding towards the outer walls of aneurysm A while segments proximal thereof (e.g. segments 11, 13) continue to be distally translated by delivery tube 30 deeper into the aneurysm A. Segment 12 in FIG. 4A is beginning to take a generally spherical shape internal to aneurysm A as braid 10 is translated distally into aneurysm A, further away from catheter 20.

Figure 4B:
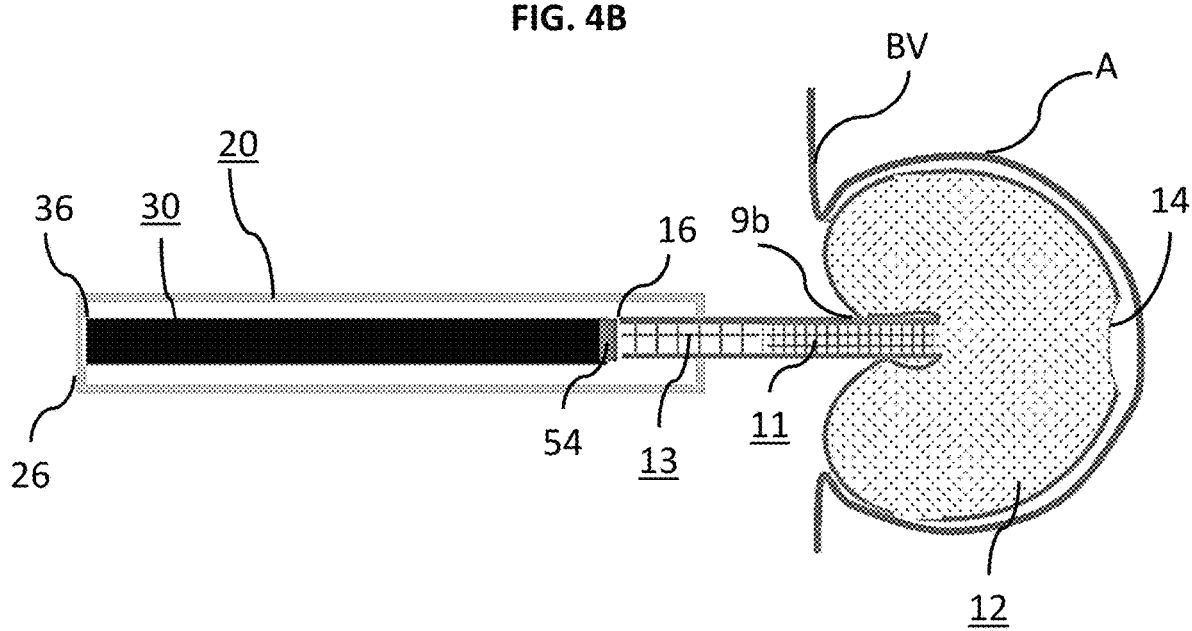
FIG. 4B is an enlarged schematic side view of the delivery system and braid of FIGS. 1-3 as the braid is being pushed into an example aneurysm.

In FIG. 4B, delivery tube 30 distally moves deeper into the aneurysm A. In turn, the inflection point 9b disposed between segments 11 and 12 causes segment 12 to buckle. By buckling, the portions of segment 12 adjacent the neck of aneurysm A are caused to bend or otherwise contour distally away from inflection point 9b. As illustrated, portions of segment 12 bow about segment 11 to the desired expanded, occlusion setting after segment 12 has buckled.

Figure 5A:
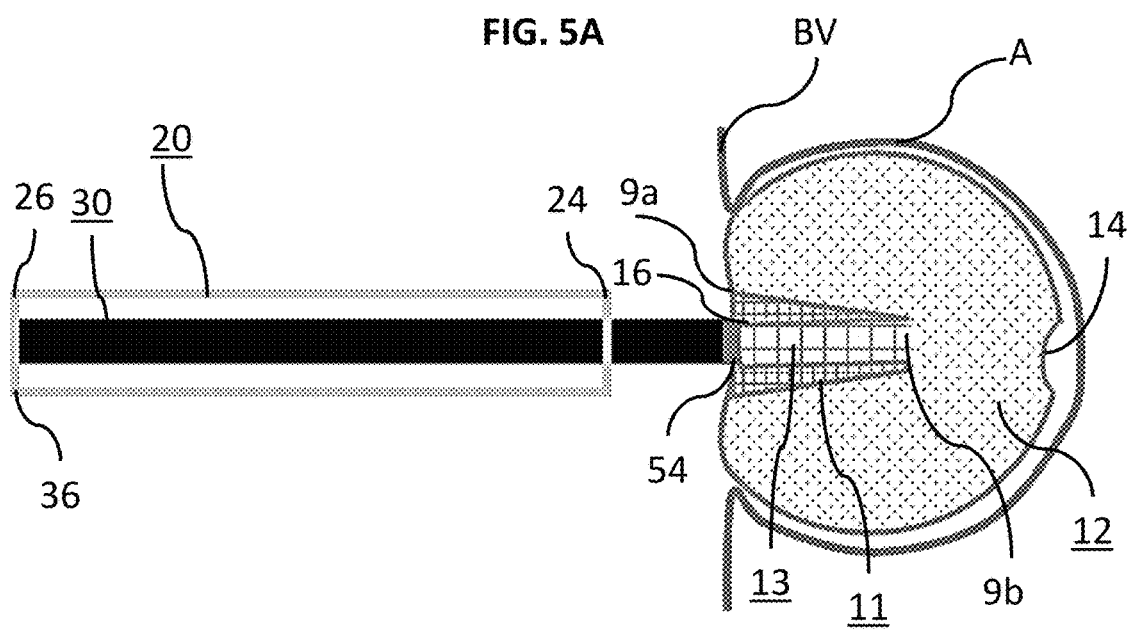
FIG. 5A is an enlarged schematic side view of the delivery system and braid of FIGS. 1-3 as the braid is being pushed and inverted into an example aneurysm.

In FIG. 5A, delivery tube 30 is further distally pushed into aneurysm A until segment 11 is fully within the distal sack of segment 12 and end 16, including locking portion 54, is at or adjacent the level of the neck of aneurysm A. In FIG. 5A, segment 11 has inverted as a result of moving distally deeper into aneurysm A after segment 12 buckled in FIG. 4B. In one example, the inversion of segment 11 into segment 12 can occur when the end 14, or extents of segment 12 of the braid 10 is relatively fixed against the wall of aneurysm A while delivery tube 30 distally pushes away from microcatheter 20. Segment 12 is also illustrated having expanded from an unexpanded state pre-deployment to the sack depicted FIG. 4B and this expansion is caused by delivery tube 30 being driven distally. Delivery tube 30 may be driven by a hypotube from its proximal end 36 by an operator or the like. The inversion of braid 10 at segments 11 and 13 can be similar to how a tube sock is configured to invert into itself. Upon inversion of segment 11 into segment 12, delivery tube 30 can continue distally pushing segment 13 into segment 11 as shown. In particular, segment 13 now moving distal of microcatheter 20 can be tucked into segment 11 in the deployed state. In certain embodiments, as segment 13 is distally tucked deeper into segment 11 and distal of microcatheter 20, segment 11 is caused to taper at the junction between segment 11 and segment 12. In certain embodiments, as this tapering occurs, proximal portions of segment 12 on or adjacent the neck are caused to blend and/or contour with the neck of the aneurysm thereby inducing a flow diverting effect in the vasculature.

In certain embodiments, segment 13 may only be structurally capably of tucking into segment 11 a predetermined distance and thus prevented from being tucked any deeper into the aneurysm A. For example, segment 13 may be capable of being tucked until the inflection point 9b of segments 11 and 12 is disposed on or adjacent the neck of the aneurysm. This serves as an additional safety feature of braid 10 since the distal sack of segment 12 would be prevented from expanding beyond a predetermined diameter. As illustrated in FIG. 5A where segment 13 is now distal of microcatheter 20, the inflection point 9b between segments 11 and 12 is illustrated disposed on or adjacent the neck of the aneurysm A, while the second inflection point 9a between segments 11 and 13 is disposed deeper in the aneurysm A (e.g., centrally located therein). In this respect, segment 11 is now completely inverted into the distal sack of 12 while segment 13 is completely inverted into segment 12 and distal of microcatheter 20. In some examples, proximal segment (13) is inverted and tucked into the distal sack of segment 12. Locking portion 54, and/or portions of delivery tube 30 can be at the level of the neck of the aneurysm A as seen under fluoroscopy. Delivery tube 30 can distally slide braid 10 until end 16 and/or locking portion 54 are tucked into the aneurysm A.

Microcatheter 20 may remain relatively stationary or fixed during the example delivery shown in FIGS. 4A-5B. Since segments 11, 12, and 13 can include different braid properties, including flexibility and/or porosity, inverting segment 11 into segment 12 and/or tucking segment 13 into inverted segment 11 is particularly advantageous. For example, inversion of segment 11 and/or tucking segment 13 prevents braid 10 from creating a protrusion that would otherwise extend into the parent vessel. Instead, any such protrusion is now inverted and tucked into the distal sack of braid 10 in the aneurysm A. Inverting segment 11 and/or tucking segment 13 can also prevent braid 10 from otherwise rupturing the aneurysm A when moving to the deployed state.

It is understood that inflection points 9a, 9b may be formed into the interstices of braid 10 between segments 11, 12, 13 so that buckling of segment 12 and/or inversion of segment 11 occurs after braid 10 has distally translated a predetermined distance outside of microcatheter 20. For example, distally translating braid 10 a first distance, with respect to the aneurysm A, can cause segment 12 to buckle about the neck of the aneurysm. Distally translating the braid a second distance, with respect to the aneurysm A, can cause segment 11 to invert into segment 12. Points 9a, 9b may be one or more weakened regions, areas, or buckling points pre-set for a particular sized distal sack. Alternatively, no inflection points 9a, 9b may be included and instead braid 10 may buckle, invert and fold into itself upon end 14 of braid contacting the dome of aneurism A (e.g. based on pre-selected flexibility of braid 10 and/or heat setting the braid in a particular manner).

Figure 5B:
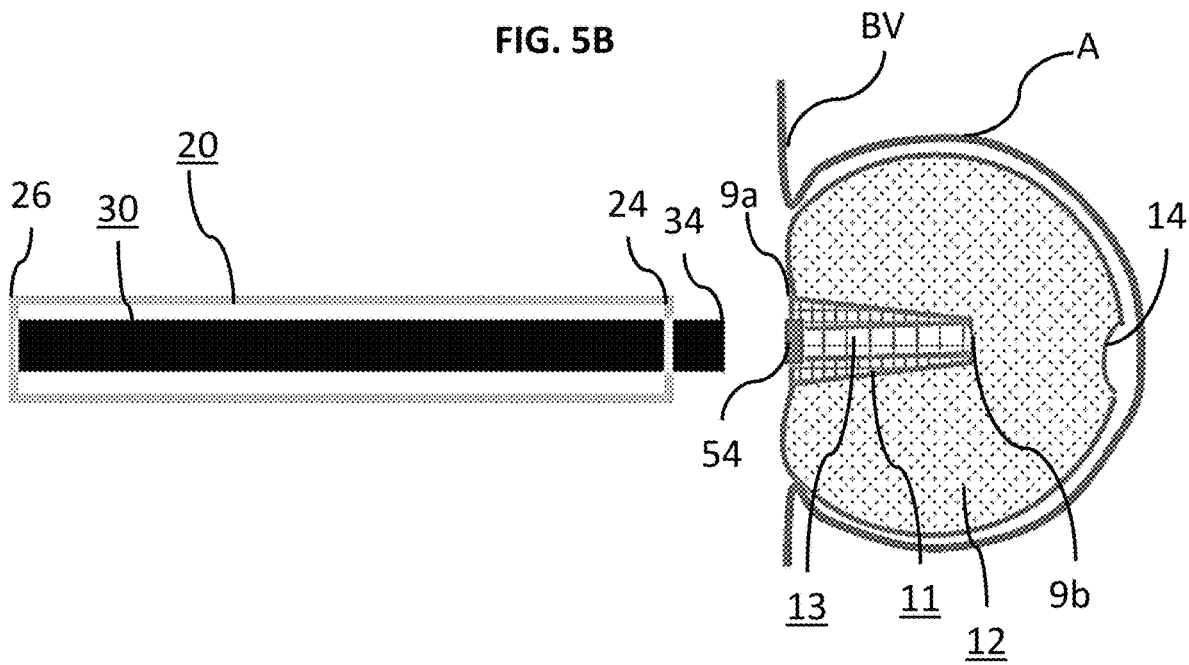
FIG. 5B is an enlarged schematic side view of the delivery system and braid of FIGS. 1-3 after the braid is deployed into an example aneurysm.

Once segments 11, 12, and 13 are selectively positioned and arranged to the desired condition (e.g. braid 10 has been translated distally into aneurysm A to expand segment 12 to form its sack, buckle, segment 11 has been inverted, and segment 13 tucked therein), braid 10 can be detached from the delivery tube 30 as shown in FIG. 5B. In particular, FIG. 5B illustrates the distal sack of segment 12 fully formed in a manner sufficient to occlude aneurysm A. However, if the sack of segment 12 is not precisely positioned or if segment 12 and/or any internally disposed segments proximal thereto need to be reset or adjusted within aneurysm A, braid 10, including segments 11, 12, and 13, can be retracted back into microcatheter 20 by proximally withdrawing delivery tube 30 back into microcatheter 20 while still attached to braid 10. In FIG. 5A, since the sack of segment 12 has been selectively positioned and formed within aneurysm A, delivery tube 30 can be proximally translated back into microcatheter 20 and both can be retracted from the braid 10 and aneurysm A.

Figure 6A:
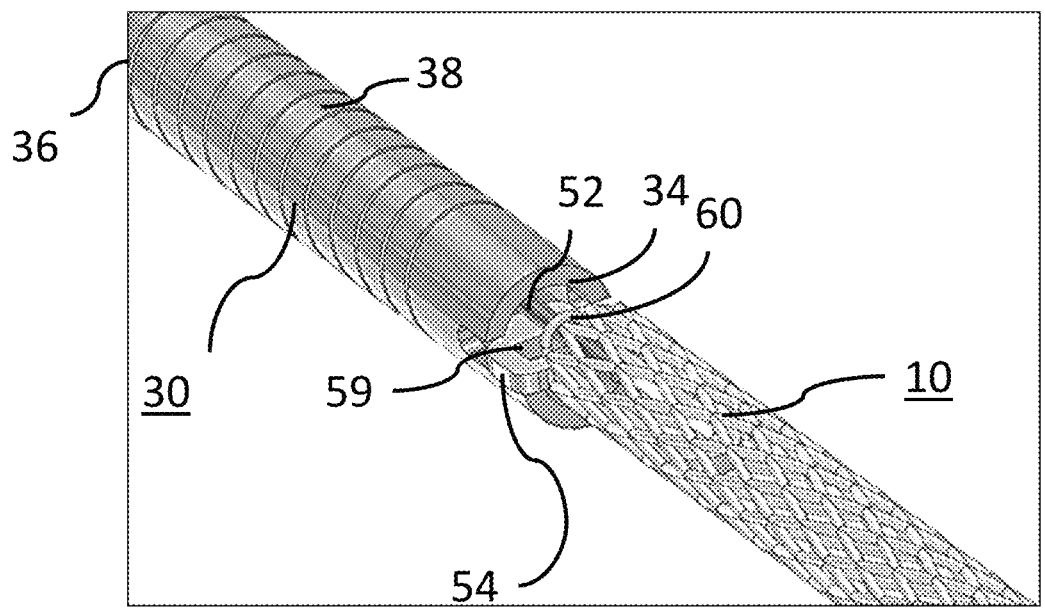
FIG. 6A is a perspective schematic view showing an exemplary delivery system for use with an example occlusive device.

FIGS. 6A to 7B generally illustrate example attachment and delivery between delivery tube 30 and braid 10 for deploying and detaching braid 10 in aneurysm A. The embodiments of FIGS. 6A to 7B is merely one way that delivery tube 30 and braid 10 may be attached at end 34 and any number of attachment means are contemplated as needed or required. The delivery tube 30 as shown can have a lumen extending from a proximal end 36 to a distal, delivery end 34. FIG. 6A illustrates braid 10 engaged with the locking member 52 and loop wire 58 locked into the locking portion 54. The opening 59 of the loop wire 58 can be placed through the locking portion 54. The locking portion 54 preferably takes the form of a small diameter elongate filament, however, other forms such as wires or tubular structures are also suitable. While the locking portion 54 is preferably formed of nitinol, other metals and materials such as stainless steel, PTFE, nylon, ceramic or glass fiber and composites may also be suitable. Locking member 52, in one example, may be an elongated retractable fiber that may extend between ends 24 and 26 of the microcatheter 20. Locking member 52 preferably takes the form of a small diameter elongate filament, however, other forms such as wires or tubular structures are also suitable. While the locking member 52 is preferably formed of nitinol, other metals and materials such as stainless steel, PTFE, nylon, ceramic or glass fiber and composites may also be suitable. When the locking member 52 is put through the opening 59 the braid 10 is now secure. It is understood that delivery tube 30 may include a compressible portion 38 disposed between its ends 34 and 36.

The compressible portion 38 can allow the delivery tube 30 to bend and/or flex. Such flexibility can assist tracking the braid 10 through the microcatheter 20 and the tortuous path through the vasculature. The compressible portion 38 can be formed with interference spiral cuts that can allow for gaps to permit bending but in one example, do not act as a spiral-cut spring. Compressible portion 38 can be axially adjustable between an elongated condition and a compressed condition. However, any other arrangement allowing axial adjustment (e.g., a wound wire or spiral ribbon) can also be suitable for use with detachment systems according to the present disclosure). The compressible portion 38 can be in the elongated condition at rest and automatically or resiliently returns to the elongated condition from a compressed condition, unless otherwise constrained. The function of the compressible portion 38 is described in greater detail herein.

Figure 6B:
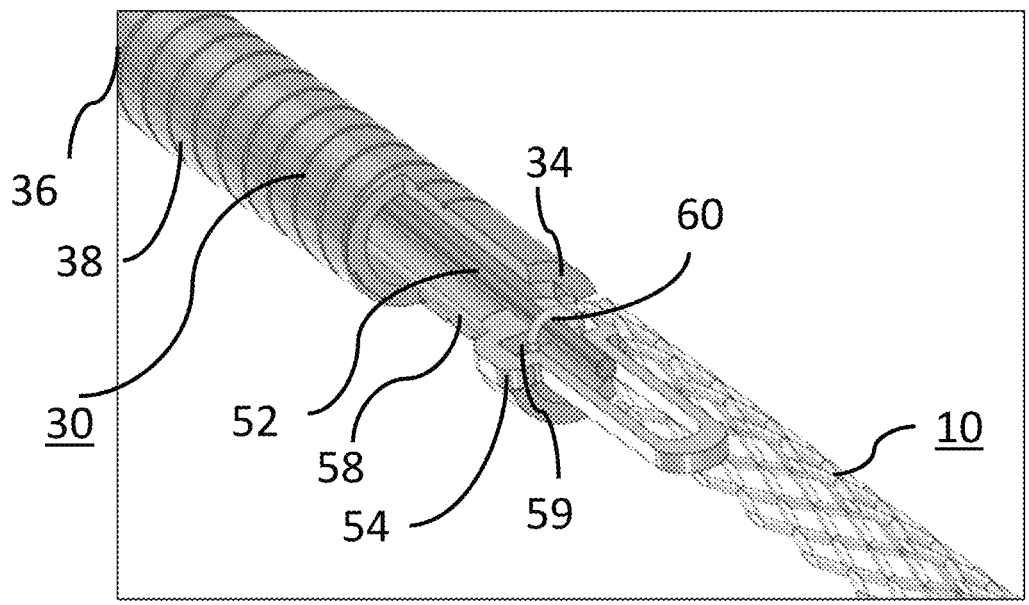
FIG. 6B is a perspective schematic view of FIG. 6A but with partial cross-section of the delivery system and the occlusive device.
Figure 7A:
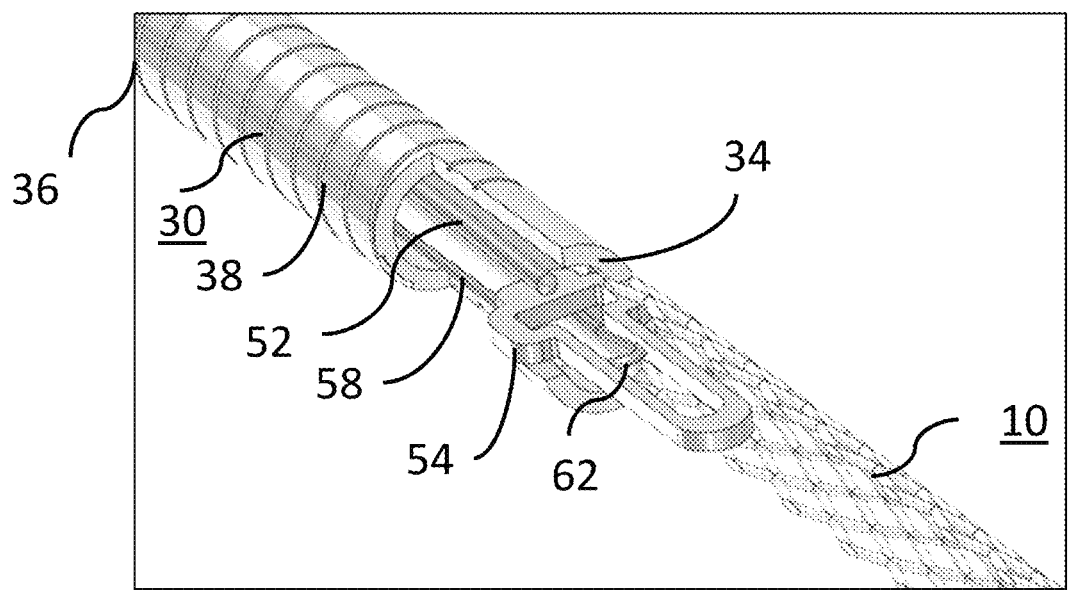
FIG. 7A is a perspective schematic view of FIGS. 6A-6B being deployed with partial cross-section of the delivery system and the occlusive device.
Figure 7B:
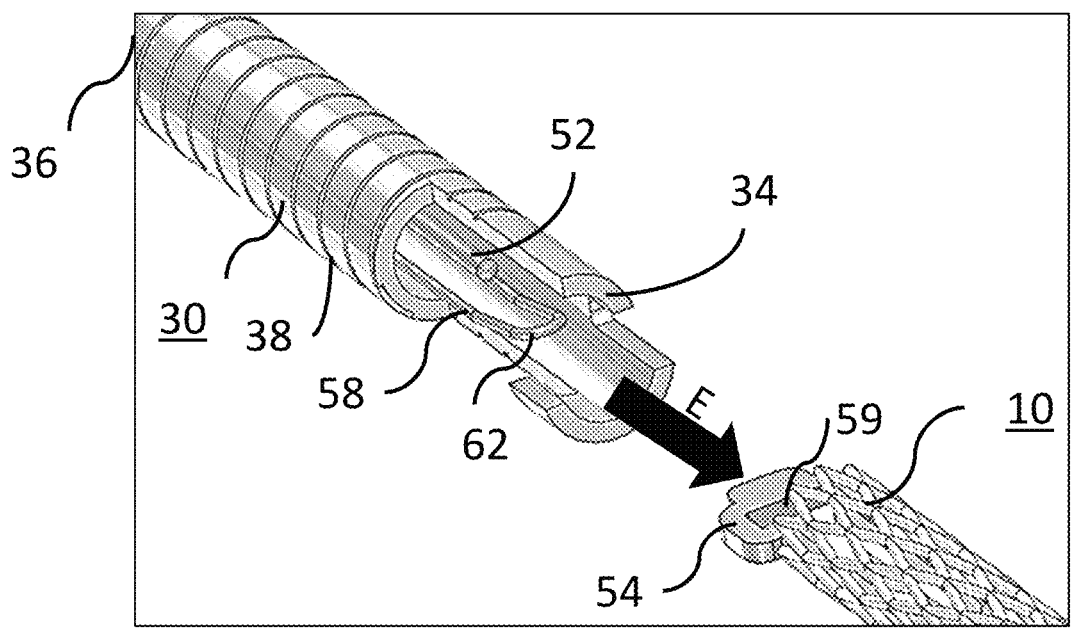
FIG. 7B is a perspective schematic view of FIGS. 6A-6B deployed with the exemplary delivery system detached from the occlusive device.

A force F was previously applied to place the delivery tube 30 in a compressed state. FIG. 6B illustrates the locking member 52 being drawn proximally to begin the release sequence for braid 10. FIG. 7A illustrates the instant the locking member 52 exits the opening 59 and is pulled free of the loop wire 58. The distal end 62 of the loop wire 58 falls away/returns to its preformed shape and exits the locking portion 54. As can be seen, there is now nothing holding the braid 10 to the delivery tube 30. FIG. 7B illustrates the end of the release sequence. Here, the compressible portion 38 of the delivery tube 30 has expanded/returned to its original shape and "sprung" forward. An elastic force E is imparted by the distal end 34 of the delivery tube 30 to the braid 10 to "push" it away to insure a clean separation and delivery of the braid 10 to the aneurysm A. It is to be understood that the delivery scheme described in FIGS. 6A-7B are merely example approaches to delivery of braid 10.

FIG. 8 is a flow diagram for a method 800 of occluding an aneurysm. Step 805 includes selectively positioning a braid at or adjacent a neck of the aneurysm. Step 810 includes distally sliding the braid into the aneurysm. Step 815 includes radially expanding a distal segment of the braid to form a distal sack inside the aneurysm, the distal sack configured to occlude the aneurysm. Step 820 includes further distally sliding the braid into the aneurysm thereby buckling the distal segment buckle about the neck of the aneurysm. Step 825 includes further distally sliding the braid into the aneurysm thereby inverting a central segment of the braid into the distal segment. Step 830 includes tucking a proximal segment of the braid into the central segment. Step 835 includes releasing the braid within the aneurysm.

Method 800 can also include tucking the proximal segment into the central segment until the proximal segment is adjacent or in communication with the neck of the aneurysm; and inducing a flow diverting effect across the neck of the aneurysm. Method 800 can also include positioning a first inflection point between the distal segment and the central segment; positioning a second inflection point between the central segment and the proximal segment; buckling the distal segment about the neck of the aneurysm, by the first inflection point, when distally translating a proximal end of the braid a first distance with respect to the neck of the aneurysm; and inverting the central segment into the distal segment, by the second inflection point, by distally translating the proximal end of the braid a second distance with respect to the neck of the aneurysm.

Method 800 can also include forming the central segment with a porosity greater than a porosity of the proximal and distal segments; and forming the porosity of the distal segment greater than the porosity of the proximal segment, or vice versa. Method 800 can also include inverting the central segment into the distal segment, by the second inflection point, which causes the central segment to tuck into the distal segment.

FIG. 9 is a flow diagram for a method 900 of occluding an aneurysm. Step 905 can include positioning a braid with the delivery tube, the braid being in a collapsed state with the microcatheter. Step 910 can include selectively positioning the microcatheter, the delivery tube, and the braid at or adjacent the neck of the aneurysm. Step 915 can include distally sliding the braid, by the delivery tube, from the microcatheter into the aneurysm. Step 915 can include radially expanding a distal segment of the braid to form a distal sack inside the aneurysm, the distal sack configured to occlude the aneurysm. Step 920 can include further distally sliding the braid, by the delivery tube, thereby buckling the distal segment about the neck of the aneurysm. Step 930 can include further distally sliding the braid, by the delivery tube, thereby inverting a central segment of the braid proximal the distal segment into the distal sack. Step 935 can include tucking a proximal segment proximal the central segment into the central segment. Step 940 can include releasing the braid within the aneurysm and withdrawing the delivery tube and the microcatheter from the aneurysm.

The method 900 can also include positioning a first inflection point between the distal segment and the central segment; positioning a second inflection point between the central segment and the proximal segment; buckling the distal segment about the neck of the aneurysm, by the first inflection point, by distally translating a proximal end of the braid a first distance with respect to microcatheter; and inverting the central segment into the distal segment, by the second inflection point, by distally translating the proximal end of the braid a second distance with respect to the microcatheter.

The method 900 can also include inverting the central segment into the distal sack which creates a flow diverting effect across the neck of the aneurysm. The method 900 can also include forming each of the proximal, distal, and central segments with a different porosity. The method 900 can also include forming the central segment with a porosity greater than a porosity of the proximal and distal segments; and forming the porosity of the distal segment greater than the porosity of the proximal segment, or vice versa. The method 900 can also include tucking the proximal segment into the central segment until the proximal segment is adjacent or in communication with the neck of the aneurysm; and inducing a flow diverting effect across the neck of the aneurysm.

It is understood that variations of the braid 10 can include various materials such as nitinol, stainless steel, bio absorbable materials, and polymers. The braid wire count of interstices of braid 10 that may form the expandable and invertible mesh can vary depending of the diameter of the sack of segment 12 and/or segments proximal thereof and/or inverted internal thereto. For example, to induce formation of the predetermined shape and strength of the distal sack of braid 10, end 14 can be opened and/or be capable of allowing for sizing or conforming to the aneurysm A. For example, if the aneurysm is relatively small, distal end 14 may close in on itself, whereas in a larger aneurysm the same braid 10 would remain open. Other segments of braid 10, including segments 11 and 13, may vary from most pliable on or about end 14 and less pliable on or about end 16. Interstices of braid 10 may also form small openings for occlusion of the aneurysm.

Braid 10, including any specific portions such as any breaks, inflection points, porosities, flexibilities, and/or corresponding sack(s), can be heat set to various configurations such as spherical, oblong, saddle shaped, etc. for the purpose of shaping the initial sack to better match the aneurysm morphology. It is also understood that any sack formed by the herein discussed braid 10 can be in a spherical shape as depicted or any other shape, as needed or required, such as ellipsoidal, heart-shaped, ovoid, cylindrical, hemispherical, or the like. Further, interstices of braid 10 that form the sack can vary, or be selectively designed, in size or shape along its length depending on how much braid 10 is caused to radially expand as delivery tube 30 is distally moved.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A braid for treating an aneurysm, the braid comprising:
   a proximal end and an open distal end;
   a distal segment disposed about the distal end, the distal segment operable to transition from a collapsed state within a microcatheter to a deployed state distal of the microcatheter whereby the distal segment radially expands to form a distal sack;
   a central segment connected to a proximal end of the distal segment; and a proximal segment connected to a proximal end of the central segment;

the central segment comprising a porosity greater than a porosity of the proximal and distal segments and the porosity of the distal segment is greater than the porosity of the proximal segment; and wherein distally translating the proximal end of the braid a first distance from within the microcatheter as the distal sack is forming distal of the microcatheter together with the different porosities of the proximal, central, and distal segments causes the proximal end of the distal segment to invert then buckle distal of the microcatheter so that the proximal end of the central segment transitions from proximal of the proximal end of the distal segment when inside the microcatheter to distal of the proximal end of the distal segment when distal of the microcatheter.

2. The braid of claim 1, further comprising an inflection point disposed between the central segment and the distal segment, wherein the proximal end is configured to be tucked inside the distal sack in the deployed state until the central segment is inverted so the inflection point is disposed adjacent the neck of the aneurysm to induce a flow diverting effect.

3. The braid of claim 1, wherein the proximal end is configured to be tucked inside the distal sack in the deployed state until the proximal end of the distal segment is disposed adjacent the neck of the aneurysm to induce a flow diverting effect.

4. The braid of claim 1, further comprising: an inflection point disposed between the proximal and distal segments.

5. The braid of claim 4, wherein the proximal segment is configured to be inverted when the inflection point is distal of the microcatheter.

6. The braid of claim 1, wherein the distal sack has a diameter at least two times greater than the microcatheter.

7. The braid of claim 1, the central segment disposed between the proximal and distal segments.

8. The braid of claim 1, further comprising:

the proximal end of the distal segment being a first inflection point; and the proximal end of the central segment being a second inflection point.

9. The braid of claim 8, the second inflection point is configured so that distally translating the braid a second distance to cause the central segment to invert then buckle into the distal segment.

10. The braid of claim 8, wherein when the first inflection point is distal of the microcatheter, the first inflection point is configured to cause the proximal end of the distal segment to invert then buckle about the neck of the aneurysm;

when the second inflection point is distal of the microcatheter, the second inflection point is configured to cause the central segment to invert then buckle into the distal segment and the proximal segment tuck into the central segment.

11. The braid of claim 8, wherein the proximal and central segment are configured to be tucked inside the distal sack in the deployed state until the first inflection point is disposed adjacent the neck of the aneurysm to induce a flow diverting effect.

12. A method of occluding an aneurysm, comprising:

selectively positioning a braid according to claim 1 at or adjacent a neck of the aneurysm;

distally sliding the braid into the aneurysm;

radially expanding the distal segment of the braid to form the distal sack inside the aneurysm, the distal sack configured to occlude the aneurysm;

further distally sliding the proximal end of the braid the first distance from outside the aneurysm then into the aneurysm as the distal sack is forming inside the aneurysm thereby causes the proximal end of the distal segment to invert then buckle inside the aneurysm so that the proximal end of the central segment transitions from proximal of the proximal end of the distal segment to distal of the proximal end of the distal segment;

further distally sliding the braid into the aneurysm thereby inverting the central segment of the braid into the distal segment; and tucking the proximal segment of the braid into the central segment.

13. The method of claim 12, further comprising:

tucking the proximal segment into the central segment until an inflection point between the distal segment and the central segment is adjacent or in communication with the neck of the aneurysm; and inducing a flow diverting effect across the neck of the aneurysm.

14. The method of claim 12, further comprising:

positioning a first inflection point between the distal segment and the central segment;

positioning a second inflection point between the central segment and the proximal segment;

buckling the distal segment about the neck of the aneurysm, by the first inflection point, when distally translating a proximal end of the braid a first distance with respect to the neck of the aneurysm; and inverting the central segment into the distal segment, by the second inflection point, by distally translating the proximal end of the braid a second distance with respect to the neck of the aneurysm.

15. The method of claim 14, wherein inverting the central segment into the distal segment, by the second inflection point, causes the central segment to tuck into the distal segment.

* * * * *